United States Patent [19]
Butter

[11] 3,981,941
[45] Sept. 21, 1976

[54] PROCESS OF MAKING LINEAR ALPHA-OLEFINS BY ETHYLENE OLIGOMERIZATION

[75] Inventor: Stephen Allan Butter, East Windsor, N.J.

[73] Assignee: Mobil Oil Corporation, New York, N.Y.

[22] Filed: Oct. 1, 1975

[21] Appl. No.: 618,531

[52] U.S. Cl. ................................. 260/683.15 D
[51] Int. Cl.² ................................. C07C 3/20
[58] Field of Search ................... 260/683.15 D

[56] References Cited
UNITED STATES PATENTS 3,574,782  4/1971  Bearden et al. .......... 260/683.15 D
3,686,350  8/1972  Yamada et al. .......... 260/683.15 D Primary Examiner—C. Davis
Attorney, Agent, or Firm—Charles A. Huggett

[57] ABSTRACT

A process for making linear alpha-olefins by oligomerization of ethylene in the presence of a catalyst comprising titanium halide-organoaluminum halide (e.g., titanium tetrachloride-ethylaluminum dichloride) and a halogenated phosphorus compound (e.g., $PCl_3$) provides oligomers of high alpha-purity and high selectivity to linear alpha-olefins with excellent control of product molecular weight.

15 Claims, No Drawings

PROCESS OF MAKING LINEAR ALPHA-OLEFINS BY ETHYLENE OLIGOMERIZATION

CROSS-REFERENCE TO RELATED APPLICATIONS

None.

BACKGROUND OF THE INVENTION

1. Field of the Invention

This invention relates to a low temperature ethylene oligomerization process for preparing linear alpha-olefins having a narrow molecular weight distribution, in the presence of a catalyst system comprising (1) titanium halide (2) organoaluminum halide and (3) a halogenated phosphorus compound.

2. Description of the Prior Art

It is known to prepare olefins by "ethylene growth", wax cracking and n-paraffin dehydrogenation. However, wax cracking and dehydrogenation result in low yields and poor quality of specific alpha-olefins.

A more widely used process based on "ethylene growth" (Ziegler) technology utilizes triethylaluminum at elevated pressures (e.g., 1500 psi) and high temperatures (ca. 200°C). A drawback of this process is the wide range ($C_4$–$C_{30}+$) of olefins produced with product maximization about $C_{12}$–$C_{14}$.

U.S. Pat. No. 3,574,782 and U.S. Pat. No. 3,652,705 disclose catalytic, low temperature (ca. −30° to +80°C) ethylene oligomerization based on titanium and alkyl aluminum catalysts. More specifically, U.S. Pat. No. 3,574,782 is directed to titanium-aluminum catalysts modified by a phosphine or phosphite and U.S. Pat. No. 3,652,705 is directed to titanium-aluminum catalysts modified by tertiary phosphines, ketones, esters, nitriles, ethers, amines and organic sulfur compounds.

SUMMARY OF THE INVENTION

In accordance with this invention, there is provided a low temperature (e.g. 20°C), low pressure (e.g., 500 psig) process for selectively making linear alpha-olefins by oligomerization of ethylene in the presence of a hydrocarbon solvent and a catalyst comprising a mixture of titanium halide (e.g., $TiCl_4$), organoaluminum halide (e.g., ethyl $AlCl_2$), and a halogenated phosphorus compound (e.g., $PCl_3$ or $PBr_3$) which result in high yields, high alpha-purity and high selectivity to linear alpha-olefins with excellent control of product molecular weight.

DESCRIPTION OF SPECIFIC EMBODIMENTS

This invention is, therefore, more particularly directed to an improved process for oligomerizing ethylene to linear alpha-olefins utilizing a titanium halide-organoaluminum halide oligomerization catalyst, the improvement comprising carrying out said process in the presence of a halogenated phosphorus compound of the following general formula:

$$(R)_y P (X)_{n-y}$$

in which X is halogen, n is 1–5 and R is aryl with y being 0, 1 or 2 thereby enhancing control of the product oligomers to a narrow molecular weight range of linear alpha-olefins.

The hereindisclosed process is accordingly directed to ethylene oligomerization under reaction conditions, controlled to produce high concentrations of low molecular weight linear alpha-olefins, conducted in the presence of a catalyst consisting essentially of titanium halide, organoaluminum halide and a halogenated phosphorus compound. More specifically, the present invention is directed to ethylene oligomerization comprising contacting ethylene with a sufficient amount of a catalyst prepared by reacting, for example, titanium tetrachloride, $C_1$–$C_{10}$ alkyl aluminum halide (e.g., ethylaluminum dichloride) and a phosphorus halide (e.g., $PCl_3$) thereby promoting the control of ethylene growth to a substantially alpha-pure, highly linear, low molecular weight alpha-olefin product. Linearity or alpha-purity represents the fraction of alpha olefins in the total olefin product, i.e.

$$\frac{\text{alpha-olefins}}{\text{alpha + branched + isomerized olefins}} \times 100 \ .$$

Catalyst composition, relative mole ratio of catalyst components, temperature, pressure and solvent properties are all important considerations, if the desired selectivity is to be obtained.

With respect to the solvent, aromatic or halogenated aromatic solvents are preferred; especially preferred is a polar solvent such as chlorobenzene. However, any suitable hydrocarbon solvent may be used. A non-limiting list of suitable solvents or diluents includes halogenated aromatics such as chlorobenzene, dichlorobenzene, chlorotoluene and the like and aromatics such as benzene, toluene, xylene, tetrahydronaphthalene and the like. Such solvents as dichloromethane, dichloroethane, and the like, may also be advantageously used. Mixtures of these and other solvents are also suitable, such as for example, an aliphatic or naphthenic solvent mixed with a polar solvent which comprises at least 40–50% wt. of the solvent based on the weight of the total solvent mixture.

The process is carried out under pressure sufficient to both maintain ethylene solubility, and to inhibit branching of the olefinic products. Pressures between about 150 and 1000 psig are highly suitable. Preferred pressures are those between about 200 and 500 psig.

The reaction is usually carried out at temperatures between about −50°C and about +60°C. Preferred temperatures arrange from about −5° to +20°C. As reaction temperature is raised, the average molecular weight of the product is also raised. Conversely, lower temperatures generally, other conditions being equal, result in lower molecular weight alpha-olefins. Accordingly, temperature is perhaps the single most important variable controlling number average molecular weight ($\overline{M}n$) of product or peaking of the alpha-olefin distribution for a particular catalyst system. For example, with $TiCl_4$, diethylaluminum chloride/$AlCl_3$, lowering reaction temperatures from 15°C to about 5°C, reduced $\overline{M}n$ from 88 to about 75. Similarly with $TiCl_4$/ethylaluminum dichloride $\overline{M}n$ was reduced from about 111 at 15°C to about 90 at 5°C.

The process is thus carried out at selected conditions of temperature and pressure to maintain ethylene in liquid phase and to aid in controlling product molecular weight (MW). These reaction conditions are so mild (150–1000 psig, −50° to +60°C) that no special corrosion resistant materials or handling procedures are required.

The preferred mole ratio for catalyst components (e.g., $TiCl_4$/$PCl_3$/$EtAlCl_2$) has been found to be about 1 to 1 to 2 (1:1:2). At these relative mole ratios high yields of alphaolefins with about 92 to 97% selectivity in the $C_4$ to $C_{20}$ range and about 96 to 98% alpha-olefin linearity are obtained. The molar ratio of catalyst components may, however, vary from about 1 to 0.25–2 to about 2–10 (1:0.25–2:2–10).

The halogenated phosphorus compounds of the instant invention are preferably selected from the group consisting of $PCl_3$, $PBr_3$, $PCl_5$, $(C_6H_5)PCl_2$ and $(C_6H_5)_2PCl$. The organo-aluminum component of the hereindisclosed catalyst system is preferably selected from ethylaluminum dichloride (EADC), ethyl aluminum sesquichloride (EASC) and diethylaluminum chloride (DEAC). Any comparable organoaluminum halide may also be conveniently used, for example, the organo component may be $C_1$–$C_{10}$ alkyl and the halide may be chloride or bromide. The titanium halide is preferably $TiCl_4$, although $TiBr_4$, $(RO)_2 - TiCl_2$ and $(RO)TiCl_3$, where R = lower alkyl may also be used.

The catalyst may be conveniently prepared in situ, although it may also be separately prepared prior to the oligomerization. When prepared in situ, the halogenated phosphorus compound is added to a suitable reaction vessel already containing titanium halide. Thereafter, the organoaluminum halide is added to the mixture which is then sufficiently cooled before adding ethylene under pressure.

The oligomerization, in an embodiment of this invention, is usually carried out in a Hastelloy-lined autoclave with provision for heating, or cooling to about −35°C. Thus, in specific embodiment, solutions comprising titanium tetrachloride, a phoshorus halide and alkyl aluminum halide (ca. 1–2 grams total catalyst) in a hydrocarbon solvent (100 cc) are pressurized with ethylene to 500 psig with vigorous stirring. Ethylene is replenished when approximately 100 psig is absorbed while maintaining constant temperature. The reaction is usually stopped after 1–3 hours, when approximately 4000 psig total (ethylene) has been taken up. This represents about 100 grams of product. Rapid venting to atmospheric pressure, is followed by injecting about 5–10 cc of alcoholic sodium hydroxide solution to quench the reaction. The process is preferably batch or continuous with plug flow, however, a conventional continuous process may also be used.

Since reactions are generally quenched when the physical capacity of the autoclave is reached, yields of product tabulated do not truly represent catalyst efficiency. Minimum molar efficiencies of the oligomerization reactions based on moles of ethylene per total moles of catalyst ($TiCl_4/PCl_3$/Et $AlCl_2$) were about 1000 or > 3000 based on titanium; on an equivalent weight basis, this represents > 150 lbs per lb. of total catalyst.

The following examples merely illustrate the essence of the hereindisclosed invention and are intended in no way to limit the scope thereof.

EXAMPLE 1

A 300 cc Hastelloy-lined autoclave (evacuated and purged 3 times with Argon) was charged with 0.27 cc $TiCl_4$ (2.5 mmol), 1.0 cc of a chlorobenzene solution containing 2.5 mmol (millimols) $PCl_3$ and 110.2 grams of chlorobenzene solvent. A heptane solution (25 %, 3.30 cc) containing 5.0 mmol of ethylaluminum dichloride was added and the resultant catalyst solution stirred at room temperature for 15 minutes. The solution was then cooled to 0°C and ethylene added to 500 psig. continued repressuring with ethylene, maintaining an average pressure of ca. 450 psig. at an average temperature of about +20°C for approximately 2.5 hours resulted in about 3700 psig ethylene uptake and a nearly full autoclave. Ethylene uptake in this and the Examples below (here 3700 psig) was approximately equivalent to about 3–3.3 mols of ethylene. The vessel was then vented to one atmosphere and the reaction mixture quenched with 5 cc of saturated alcoholic NaOH solution. A yield of approximately 80 grams of pure alpha-olefin solution resulted. This solution was analyzed with VPC (vapor phase chromatography) showing the following distribution of pure, linear alpha-olefins: approximate wt. % selectively $C_4H_8$ (11.9), $C_6H_{12}$ (15.7), $C_8H_{16}$ (17.7), $C_{10}H_{20}$ (14.9), $C_{12}H_{24}$ (12.4), $C_{14}H_{28}$ (11.7), $C_{16}H_{32}$ (5.3), $C_{18}H_{36}$ (7.0), $C_{20}H_{40}$ (3.3).

EXAMPLE II

The procedure of Example I was followed; a 300 cc Hastelloy-lined autoclave was charged with 2.5 mmol of $TiCl_4$, 1.25 mmol of $PCl_3$ and 5 mmol of ethylaluminum dichloride. Pressure was maintained at about 450 psig and temperature averaged °20°C. A yield of approximately 75 grams of pure alpha-olefin resulted. Analysis showed the following linear alpha-olefin distribution: approximate wt. % $C_4H_8$ (8.6), $C_6H_{12}$ (18.8), $C_8H_{16}$ (19.2), $C_{10}H_{20}$ (15.5 ), $C_{12}H_{22}$ (11.4), $C_{14}H_{28}$ (8.2), $C_{16}H_{32}$ (5.9), $C_{18}H_{36}$ (3.8), $C_{20}H_{40}$ (6.3), $C_{22+}$ (2.3). The reaction was stopped after approximately 2.5 hours. Analysis was by VPC.

EXAMPLE III

The procedure of Example I was followed; a 300 cc Hastelloy-lined autoclave was charged with 2.5 mmol of $TiCl_4$, 2.5 mmol of $PCl_5$ and 5 mmol of ethylaluminum dicloride. An average pressure of about 450 psig was maintained by continued repressuring with ethylene at an average temperature of about +10°C for approximately 2.5 hours. A yield of about 41 grams of pure alpha-olefin was obtained: approximate weight % selectivity $C_4H_8$ (16.7), $C_6H_{12}$ (22.0), $C_8H_{10}$ (19.4), $C_{10}H_{20}$ (14.5), $C_{12}H_{24}$ (11.7), $C_{14}H_{28}$ (4.9), $C_{16}H_{32}$ (4.2), $C_{18}H_{36}$ (6.5), $C_{20}H_{40}$ ( − ).

EXAMPLE IV

The procedure of Example I was followed; a Hastelloy-lined autoclave was charged with 2.5 mmol of $TiCl_4$, 2.5 mmol of $PBr_3$ and 5.0 mmol ethylaluminum dicloride. An average pressure of about 450 psig was maintained by continued repressuring with ethylene at an average temperature of about +10°C for approximately 2.5 hours. A yield of about 65 grams pure alpha-olefin resulted: approximate wt. % selectivity $C_4H_8$ (7.7), $C_6H_{12}$ (15.7), $C_8H_{16}$ (18.0), $C_{10}H_{20}$ (14.3), $C_{12}H_{24}$ (12.0), $C_{14}H_{28}$ (9.4), $C_{16}H_{32}$ (8.0), $C_{18}H_{36}$ (5.3), $C_{20}H_{40}$ (4.2), $C_{22+}$ (5.3).

EXAMPLE V

For comparison purposes, a Hastelloy-lined autoclave, similar to that of Example I, was charged with 2.5 mmol of $TiCl_4$, 2.5 mmol of tripheylphoshine and 5.0 mmol of ethylaluminum dichloride. Ethylene was then added to the reaction vessel in identical amounts and under the same conditions as in Example I. Other reaction conditions were also identical except the average temperature was 0°C. A yield of approximately 35 grams of alpha-olefins were obtained with about 25 wt. % of the product being high molecular weight waxes.

EXAMPLE VI

Also for further comparison a Hastelloy-lined autoclave was charged as follows: 2.5 mmol of $TiCl_4$, and 2.5 mmol of trimethylphoshite and 5.0 mmol of ethylaluminum dichloride. Ethylene was then added to the reaction medium in identical amounts and under the same conditions as in Example IV. Other reaction conditions were also identical. A yield of 6.5g of alpha-olefins with more than 90 wt. % of product being high MW wax.

The catalyst systems of Examples V and VI had significantly lower reaction rates than catalysts which contained a halogenated phosphorus compound in accordance with this invention. Additionally, with respect to these examples when reaction did occur as in Example V, a substantially higher MW distribution of olefins were produced giving low yields with ≳ 90% of product in higher than $C_4-C_{20}$ olefin range. Thus TiAl catalysts modified with phosphine rather than halogenated phosphorus acted as inhibitors under substantially the same process conditions embodied in the herein-disclosed invention.

Table I summarizes and compares ethylene oligomerization results obtained with various halogenated phosphorus cocatalysts, i.e., TiAl catalyst modified with a halogenated phosphorus compound. The selectivities to $C_4-C_{20}$ MW range, number average molecular weights ($\overline{Mn}$) and alpha-linearities are based on the chlorobenzene soluble portion of product. Runs 6–9 used prior art phosphorus modifiers.

producing highly linear alpha-olefin structure olefins are those catalytic systems which in accordance with the hereindisclosed invention utilize phosphorus halide, e.g., $PCl_3$, $PCl_5$, $PBr_3$ modified catalysts. The catalysts employing non-halogenated phosphorus compounds, e.g., runs 7 $Bu_3P$, and 9, $(ETO)_3P$, exhibited lower catalytic activity compared with that of said halogenated compounds and in fact in reactions under the same experimental conditions initially function as inhibitors with no appreciable reaction under after about 40 minutes in the reaction medium. Additionally successive replacement of phenyl for chlorine ($PCl_3$, $PhPCl_2$, $Ph_2PCl$, $Ph_3P$) generally results in an increase in molecular weight distribution and a decrease in alpha-linearity.

Table II is a comparison of $C_4-C_{20}$ alpha-olefins, yields and structure linearity as a function of the molecular ratio of titanium halide/halogenated phosphorus compounds/organoaluminum halide catalyst composition. Best results were obtained at a molar ratio of about 1:1:~2, see for example runs 3–5 of said Table. Higher phosphorus levels usually adversely affect MW distribution and alpha-linearity. However, when the halogenated phosphorus compound is a chloride, e.g., $PCl_3$, $PCl_5$, only the reaction rate and not MW or alpha-purity were effected. Consequently the preferred halogenated phosphorus compound for use in the disclosed and claimed catalyst system is phosphorus chloride and more particularly $PCl_3$. Linearity or alpha-olefin purity was about 96–97%, i.e., 96–97% of the olefins obtained by the hereinembodied oligomerization process are alpha-olefins with about 92–93% of the oligomers in the $C_4-C_{20}$ range. Higher phosphorus halide to titanium

TABLE I

EFFECT OF VARIOUS PHOSPHORUS-PROMOTED CATALYSTS ON LINEARITY OF $C_4-C_{20}$ MW RANGE OLEFINS

| RUNS* | MODIFIER | %$C_4-C_{20}$ | MW[1] | ALPHA-LINEARITY |
|---|---|---|---|---|
| *According to the Invention* | | | | |
| 1 | $PCl_3$ | 92–97 | 119 | > 90% |
| 2 | $PCl_5$ | 94–99 | 103 | > 90% |
| 3 | $PBr_3$ | 95–98 | 105 | > 90% |
| 4 | $PhPCl_2$ | 97 | 112 | ca. 85% |
| 5 | $Ph_2Cl$ | 90 | 123 | ca. 75% |
| *Prior Art* | | | | |
| 6 | $Ph_3P$ | > 75 | — | ca. 85% |
| 7 | $Bu_3P$ | < 30 | — | ca. 85% |
| 8 | $(C_8)_3P$ | 66 | >126 | — |
| 9 | $(EtO)_3P$ | <40 | — | — |
| 10 | $(MEO)_3PO$ | NR[2] | — | — |

CATALYST: $TiCl_4$/P/EtAlCl$_2$ molar ratio of components = 1:1:2 except for the following: run 8 molar ratio = 1:2:1; run 9 molar ratio = 1:0:1:1 and run 10 molar ratio was 1:0.2:1.
PRESSURE: Approx. 450 psig.
TEMPERATURE: 10°C for runs 2–5; 0°C for runs 7–10; –5 to +20°C for run 1, average of several runs
SOLVENT: Chlorobenzene — all runs

[1]Calculated as in U.S. 3,574,782.
[2]NR = reaction after about 35–45 minutes.
*Runs 1, 2, 3, 7, 8 and 10 are the average of two or more runs.

From the data of Table I it is apparent that of the various TiAl catalyst systems tested under substantially identical conditions the best for controlling MW and levels, i.e. >~2:1, were also found to lower the reaction rate of the oligomerization process.

TABLE II

ETHYLENE OLIGOMERIZATION WITH PHOSPHORUS HALIDE MODIFIED CATALYSTS $C_4-C_{20}$ ALPHA-OLEFIN YIELDS AND PURITY

| RUN NO. | mmols $TiCl_4$/ | $PX_nPCl_3$/ | EADC | % ALPHA-LINEARITY | $C_4-C_{20}$ | YIELD (g)[2]/TIME (min) |
|---|---|---|---|---|---|---|
| 1 | 1.25 | .25 | 2.5 | 86.6 | 93.7 | 95/128 |
| 2 | 1.25 | 0.625 | 2.5 | 96.4 | 92.8 | 75/143 |
| 3 | 1.25 | 1.25 | 2.5 | 97.1 | 92.3 | 75/158 |
| 4 | 2.5 | 2.5 | 5.0 | 97.0 | 96.5 | 80/140 |

TABLE II-continued
ETHYLENE OLIGOMERIZATION WITH PHOSPHORUS HALIDE MODIFIED CATALYSTS
$C_4$-$C_{20}$ ALPHA-OLEFIN YIELDS AND PURITY

| RUN NO. | mmols TiCl$_4$/ | PX$_n$PCl$_3$/ | EADC | % ALPHA-LINEARITY | $C_4$-$C_{20}$ | YIELD (g)$^2$/TIME (min) |
|---|---|---|---|---|---|---|
| 5 | 2.5 | 5.0 | 5.0 | 98 | 92 | 10/115 |
|   |     | PBr$_3$ |   |   |   |   |
| 6 | 2.5 | 2.5 | 5.0 | 85.7 | 75 | 90/128 |
| 7 | 2.5 | 2.5 | 5.0 | 98.0 | 96.8 | 41/26 |
| 8 | 1.25 | 1.25 | 2.5 | 85.7 | 79 | 52/186 |
| 9 | 2.5 | 2.5 | 5.0 | 74.3 | 95 | 110/51 |
| 10 | 2.5 | 2.5 | 5.0 | 95 | 94 | 65/90 |
| 11 | 2.5 | 5.0 | 5.0 | 98.3 | 98 | 45/135 |
|   |     | UNMODIFIED |   |   |   |   |
| 12 | 2.5 | 0 | 5.0 | 72.9 | 95 | 59/54 |
| 13 | 2.5 | 0 | 2.5 | 72.5 | 95 | 77/90 |

All Runs: Temp. 10°C, Pressure 450 psig, Solvent — chlorobenzene.
n = 3 or 5
EADC = Ethylaluminum dichloride Unmodified titanium-aluminum catalysts were found to generally give poor alpha-linearity and poor temperature control characteristics with more frequent erratic exotherms under otherwise equivalent conditions than the halogenated phosphorus modified catalytic system disclosed and claimed herein. Thus, even where process conditions were such that methods utilizing unmodified catalyst systems obtained peaking at low molecular weights, alpha-linearity was poor. Additionally, the phosphorus halides as embodied herein such as for example PCl$_3$, PBr$_3$, and PCl$_5$ are also less deactivating (i.e. inhibiting) than phosphines (PR$_3$) and phosphites [P(OR)$_3$]. Additionally, under the disclosed conditions of temperature and pressure carbon-number peaking generally occured for catalysts containing a halogentated phoshorus compound according to this invention at low carbon number, i.e., at about $C_6$-$C_{10}$, see Table III.

Table III compares the alpha-olefin selectivities of the various preferred halogenated phosphorus compounds, i.e., PCl$_3$, PCl$_5$ and PBr$_3$ exemplifying $C_4$-$C_{22}$+ distribution. As noted above, these preferred modifiers result in carbon-number peaking in the $C_6$-$C_{10}$ range (Runs 1 and 2 peaking at $C_8$).

Accordingly, the novel use of halogenated phosphorus TiAl catalyst systems provides linear alpha-olefin product with better MW control, higher yields, and higher selectivity to linear alpha-olefins of low molecular weight. The use of such phosphorus halides tend also to reduce branching and olefin-isomers thereby resulting in further selectivity to alpha-olefins as compared with unmodified titanium-aluminum catalysts and also by controlling reaction exotherms additionally promote higher yields with better control of product MW and alpha-linearity compared with prior art methods.

TABLE III
ALPHA-OLEFIN SELECTIVITY (WT. %) P-HALIDE MODIFIED ETHYLENE OLIGOMERIZATIONS

| RUNS | 1 TiCl$_4$/PCl$_3$/EADC | 2 TiCl$_4$PCl$_3$/EADC | 3 TiCl$_4$PCl$_5$/EADC | 4 TiCl$_4$/PBr$_3$/EADC |
|---|---|---|---|---|
| $C_4$ | 8.6 | 6.3 | 16.7 | 15.6 |
| $C_6$ | 18.8 | 13.2 | 22.0 | 23.8 |
| $C_8$ | 19.2 | 14.2 | 19.4 | 19.5 |
| $C_{10}$ | 15.5 | 13.2 | 14.5 | 14.4 |
| $C_{12}$ | 11.4 | 11.7 | 11.7 | 10.3 |
| $C_{14}$ | 8.2 | 10.0 | 4.9 | 7.7 |
| $C_{16}$ | 5.9 | 8.4 | 4.2 | 4.3 |
| $C_{18}$ | 3.8 | 6.6 | 6.5 | 3.1 |
| $C_{20}$ | (6.3) | 5.9 | — | 1.4 |
| $C_{22+}$ | 2.3 | 10.6 | — | — |

Although the present invention has been described with preferred embodiments, it is to be understood that modifications and variations may be resorted to while not departing from the spirit and scope of the invention.

What is claimed is:

1. In a process for oligomerizng ethylene to linear alpha-olefins utilizing a titanium halide-organoaluminum halide oligomerization catalyst, the improvement comprising carrying out said process in the presence of a halogenated phosphorus compound of the following general formula:

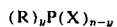

$$(R)_y P(X)_{n-y}$$

in which X is halogen, n is 1–5 and R is aryl with y being 0, 1 or 2 thereby enhancing control of the product oligomers to a narrow molecular weight range of linear alpha-olefins.

2. The process of claim 1 wherein said process is carried out in the presence of an aromatic or halogenated aromatic hydrocarbon solvent.

3. The process of claim 1 wherein the temperature is from about −50° to +60°C.

4. The process of claim 3 wherein the temperature is from about −5° to +20°C.

5. The process of claim 1 wherein the pressure is from about 150 to about 1000 psig.

6. The process of claim 5 wherein the pressure is from about 200 to 500 psig.

7. The process of claim 1 wherein the titanium halide is titanium tetrachloride.

8. The process of claim 1 wherein the organoaluminum halide is selected from the group consisting of $C_1$–$C_{10}$ alkyl aluminum halide, alkyl aluminum dihalide or alkyl aluminum sesquihalide.

9. The process of claim 8 wherein the halide function of the said organoaluminum halide is chloride.

10. The process of claim 1 wherein the halogenated phosphorus compound is selected from the group consisting of $PCl_3$, $PBr_3$, $PCl_5$, $(C_6H_5)PCl_2$ and $(C_6H_5)_2PCl$.

11. The process of claim 1 wherein the titanium halide is titanium tetrachloride, the organoaluminum halide is selected from the group consisting of a $C_1$–$C_{10}$ alkyl aluminum chloride, alkyl aluminum dichloride or alkyl aluminum sesquichloride and the halogenated phosphorus compound is selected from the group consisting of $PCl_3$, $PBr_3$, $PCl_5$, $(C_6H_5)PCl_2$ and $(C_6H_5)_2PCl$.

12. The process of claim 11 wherein the organoaluminum compound is ethyl aluminum dichloride and the halogenated phosphorus compound is $PCl_3$.

13. The process of claim 11 wherein said process is carried out in the presence of an aromatic or halogenated aromatic, hydrocarbon solvent.

14. The process of claim 13 wherein the solvent is chlorobenzene.

15. The process of claim 11 wherein the temperature is from about −5° to +20°C and the pressure is from about 200 to 500 psig.

* * * * *

UNITED STATES PATENT AND TRADEMARK OFFICE
CERTIFICATE OF CORRECTION

PATENT NO. : 3,981,941
DATED : September 21, 1976
INVENTOR(S) : STEPHEN ALLAN BUTTER It is certified that error appears in the above–identified patent and that said Letters Patent are hereby corrected as shown below:

| | |
|---|---|
| Col. 1, line 19 | "n-paraffin" should be --$\underline{n}$-paraffin--. |
| Col. 2, line 46 | "arrange" should be --range--. |
| Col. 4, line 1 | "continued" should be --Continued--. |
| Col. 4, line 25 | "°20°C" should be --+20°C--. |
| Col. 5, line 20 | "$\lesssim$" should be -- $\gtrsim$ --. |
| Col. 5, Table I | "(2)NR = reaction after about 35-45 minutes" should be --(2)NR = no reaction after about 35-45 minutes--. |

Signed and Sealed this

First Day of February 1977

[SEAL]

Attest:

RUTH C. MASON
Attesting Officer

C. MARSHALL DANN
Commissioner of Patents and Trademarks